United States Patent
Sasajima et al.

(10) Patent No.: US 7,288,764 B2
(45) Date of Patent: Oct. 30, 2007

(54) PATTERN MEASURING METHOD

(75) Inventors: Fumihiro Sasajima, Hitachinaka (JP);
Yoshihiro Kimura, Hitachinaka (JP);
Osamu Komuro, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 11/651,498

(22) Filed: Jan. 10, 2007

(65) Prior Publication Data

US 2007/0114399 A1    May 24, 2007

Related U.S. Application Data

(63) Continuation of application No. 11/066,219, filed on Feb. 28, 2005, now Pat. No. 7,180,062.

(30) Foreign Application Priority Data

Mar. 26, 2004    (JP) ............................ 2004-092987

(51) Int. Cl.
*H01J 37/49*    (2006.01)
(52) U.S. Cl. .................................... 250/310

(58) Field of Classification Search ................ 250/310, 250/306, 307
See application file for complete search history.

(56) References Cited

U.S. PATENT DOCUMENTS

| | | | |
|---|---|---|---|
| 6,839,470 B2 | 1/2005 | Ikeda | |
| 7,049,589 B2 | 5/2006 | Yamaguchi et al. | |
| 7,053,371 B2 | 5/2006 | Ojima et al. | |
| 7,180,062 B2 * | 2/2007 | Sasajima et al. | ............ 250/310 |
| 2005/0205780 A1 | 9/2005 | Nakagaki et al. | |

FOREIGN PATENT DOCUMENTS

JP    2003-037139 A    2/2003

\* cited by examiner

*Primary Examiner*—Kiet T. Nguyen
(74) *Attorney, Agent, or Firm*—McDermott Will & Emery LLP

(57) ABSTRACT

A pattern measuring method calculates an average pattern shape from a plurality of the same patterns appearing within an image captured using an electron microscope, and compares pattern information at each measuring position with average pattern information to determine roughness.

10 Claims, 6 Drawing Sheets

AVERAGE PATTERN SHAPE

COMPARE WITH AVERAGE SHAPE AND USE AS INDICATOR OF ROUGHNESS

PATTERN MEASURING METHOD

RELATED APPLICATIONS

This application is a continuation of application Ser. No. 11/066,219, filed Feb. 28, 2005, now U.S. Pat. No. 7,180,062 which is based on Japanese Patent Application No. JP 2004-092987 filed Mar. 26, 2004, the contents of which applications are hereby incorporated by reference.

BACKGROUND OF THE INVENTION

The present invention relates to a pattern measuring method for use with a scanning electron microscope which scans a specimen with electron beams and captures information on the surface of the specimen in the form of image from the amount of a secondary electron signal emitted from the specimen as a result of the scanning, and more particularly, to a method of stably measuring an average line width of a pattern.

With the increasing miniaturization of semiconductor devices, the edge roughness of a pattern has become a problem. The edge roughness has been investigated in regard to how it occurs, and attempts have been made for a management based on the roughness value, and a management based on an average measured value including the edge roughness used as an indicator.

FIG. 2 shows an example of a conventional line width measuring method. An edge detecting range is set for a pattern under measurement. The profile of an image is created from image information, and the positions of edges are determined using information on the waveform of a differentiated version of the profile. The line width is determined from information on the left and right edges (in the same orientation of adjacent patterns when in a pitch measurement). A portion corresponding to a convex edge of the pattern appears in white in a SEM image. Even a straight line by design results in an undulate form, as indicated by a black wave line in the figure. The edge roughness is defined to be variations in the noted right or left edge, while a width roughness is defined to be variations in the line width measured a plurality of times in the vertical direction.

The prior art related to the foregoing pattern measurement is disclosed, for example, in JP-A-2003-37139.

The width roughness will be described with reference to FIG. 3. The measurement of a line width involves setting edge detecting areas along the two edges, as indicated by black bold lines in FIG. 3, and detecting edges within the edge detecting areas. Then, the distance between the edges is defined to be a line width in that area. However, when roughness exists as shown, the line width largely differs at a measuring position A and at a measuring position B in FIG. 3.

Possible causes for the roughness can include variations attributable to the measuring method other than variations in the shape itself. FIGS. 4A and 4B show exemplary profiles at the measuring position A and measuring position B in FIG. 3, respectively. Generally, for making measurements at a plurality of measurement points, a common parameter is set and applied to each pattern under measurement. Assume that a line width is measured with thresholds which are 30, 50, 70% of the difference between the highest point and the lowest point in a profile. When the pattern does not include any local step as shown in FIG. 4B, measured values increase at a constant rate in the order of 30%, 50% and 70%. In other words, there is a linear relationship between the threshold and the measured value. On the other hand, when a profile include local steps as shown in FIG. 4A, measured values irregularly vary depending on which of 30%, 50% and 70% threshold should be used. In other words, measured values largely vary depending on a set threshold. Since such steps can locally and sporadically appear in a pattern, measured values largely vary depending on an area used for the measurement and on a set threshold, even in a line pattern as shown in the example.

Consider that the foregoing measurement is applied to a line pattern which has local edge roughness as shown in FIG. 3. Portions represented by white bold lines are called "white bands" which correspond to the edges of the line, and include global pattern roughness. On the other hand, portions indicated by black thin lines represent the result of measurement. The latter is indicated by black thin line in order to distinguish the global pattern shape from the local roughness.

The pattern having the roughness as shown is measured at the measuring positions A and B. The luminance value is accumulated in a rectangular area (measuring area) around the measuring position A in the vertical direction to create its profile, and information on the edges at the measurement point A is acquired from the profile resulting from the accumulation. Information on the edges at the measuring position B is acquired in a similar manner. Consider now that the line width is measured from the distance between the respective edges at the measuring positions A, B. From a viewpoint of a stable measurement of the line width in the line pattern, it is desired to be able to measure the line width W, represented by the spacing between the white lines in FIG. 3, from which the influence of the roughness is omitted. However, the aforementioned method is adversely affected by the local roughness, so that a line width $W_A$ is measured at the measuring position A, while a line width $W_B$ is measured at the measuring position B, thus presenting largely differing results of measurement depending on the position set for the measurement. While the roughness is seemingly caused by a process, a material and the like, correct causes cannot have been so far identified, so that the global line width can be preferably measured separately from the roughness.

Also, conventionally, when an average line width is measured for a line or a space pattern image including edge roughness, the line width is locally measured at multiple positions, and measured values are averaged, thus implying problems of an extended processing time, instable calculated values, and the like.

SUMMARY OF THE INVENTION

It is an object of the present invention to provide a measuring method which is capable of stably measuring a line width in a simple manner separately from local roughness.

Conventional measuring techniques for measuring a line width in a pattern image involve setting a certain target, locally detecting edges within the range of the target, and measuring the line width based on information resulting from the local edge detection, so that the influence of the local edge roughness causes variations in the measured values. The present invention, on the other hand, makes a measurement on an average image of a plurality of the same patterns within the same screen, and can therefore measure the local edge roughness and global roughness, which can cause the variations, and variations in roughness in the screen. Also, when the measurement is specified for the global roughness, the local roughness of an image is averaged by superimposing a plurality of patterns within the same screen, thus reducing errors due to a particular measuring method.

To solve the foregoing problem, the pattern measuring method of the present invention measures a line width by capturing an image at a scaling factor which permits a plurality of patterns under measurement to appear within the same screen, and measuring a line width and roughness for an arbitrary pattern within the captured image using periodic information and shape information such as a line, a space, a hole, and the like under measurement. The pattern measuring method also calculates an average value for the pattern measurement from the results of measuring patterns captured at a plurality of different locations, and calculates roughness information possessed by each of the plurality of patterns within the screen.

Specifically, the pattern measuring method of the present invention includes the steps of capturing an image of a specimen at a scaling factor which permits a plurality of patterns under measurement to appear within a field of view, creating a plurality of profiles in a shape measuring area corresponding to each of the plurality of patterns under measurement, calculating an average profile by averaging the plurality of profiles created in all the shape measuring areas corresponding to the plurality of patterns under measurement, and determining a shape roughness for the shape measuring area corresponding to each pattern under measurement using the average profile and the plurality of profiles created in the shape measuring area of each pattern under measurement. When the pattern under measurement is a line or a space pattern, the width of a line or a space from the profile can be calculated from the profiles, and an average width of the line or the space is calculated from the average profile to determine width roughness as the shape roughness.

The average profile can be calculated by averaging the plurality of profiles created in the shape measuring area corresponding to each of the plurality of patterns under measurement. Alternatively, the average profile can be calculated by accumulating luminance values in the shape measuring area for each of the pattern under measurement in a direction along the line or the space to create a accumulated profile, and averaging the accumulated profiles.

Other objects, features and advantages of the invention will become apparent from the following description of the embodiments of the invention taken in conjunction with the accompanying drawings.

DETAILED DESCRIPTION OF THE INVENTION

In the following, one embodiment of the present invention will be described with reference to the accompanying drawings.

Figure 1:
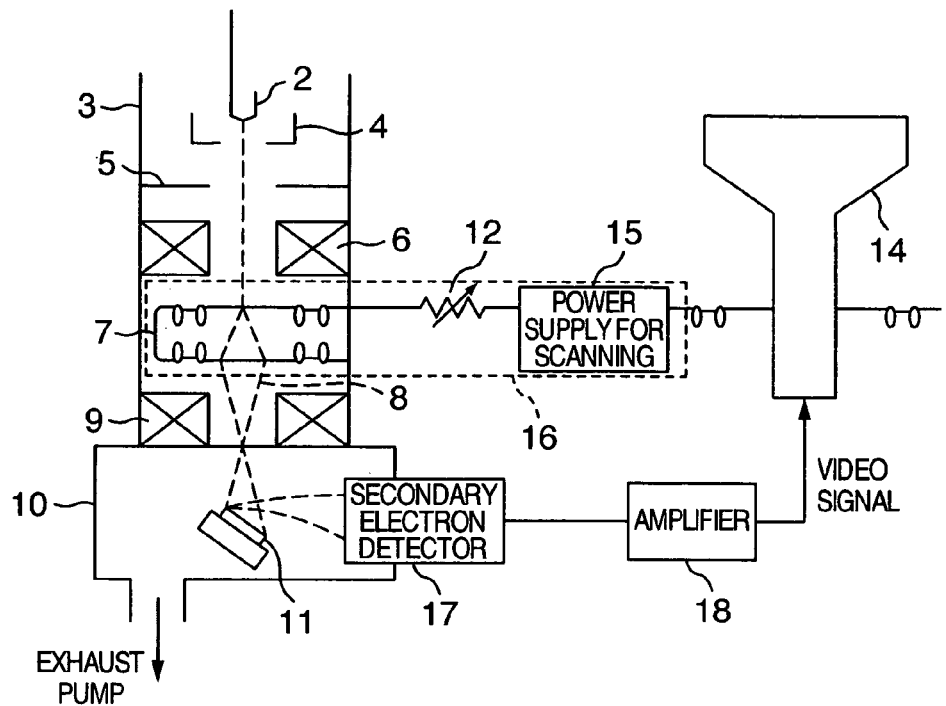
FIG. 1 is a schematic diagram illustrating an exemplary configuration of a scanning electron microscope for conducting a miniature pattern test according to the present invention.
Figure 2:
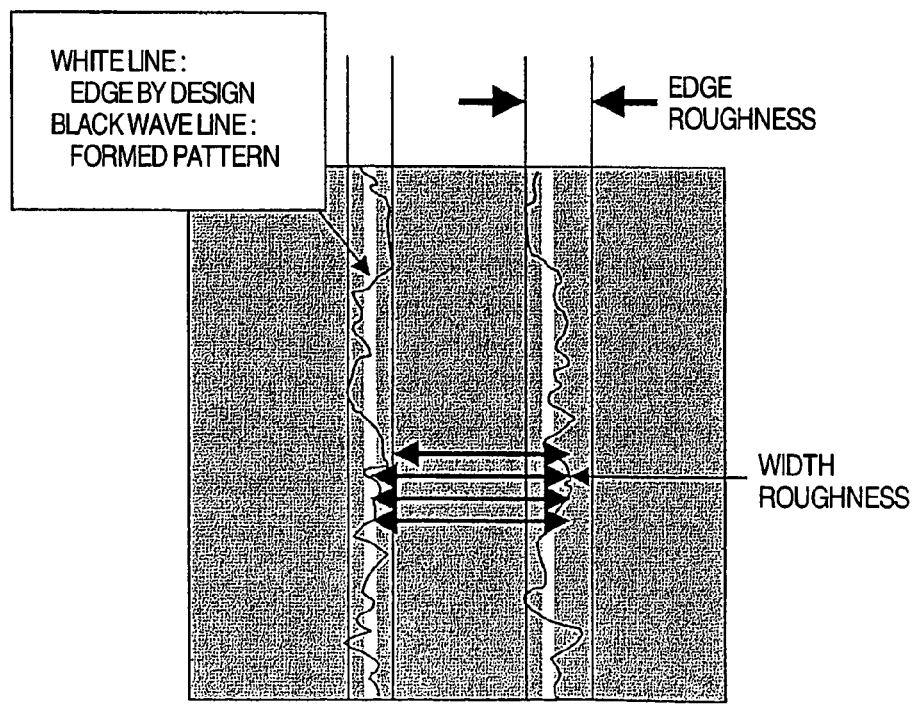
FIG. 2 is a diagram showing an exemplary conventional line width measuring method.
Figure 3:
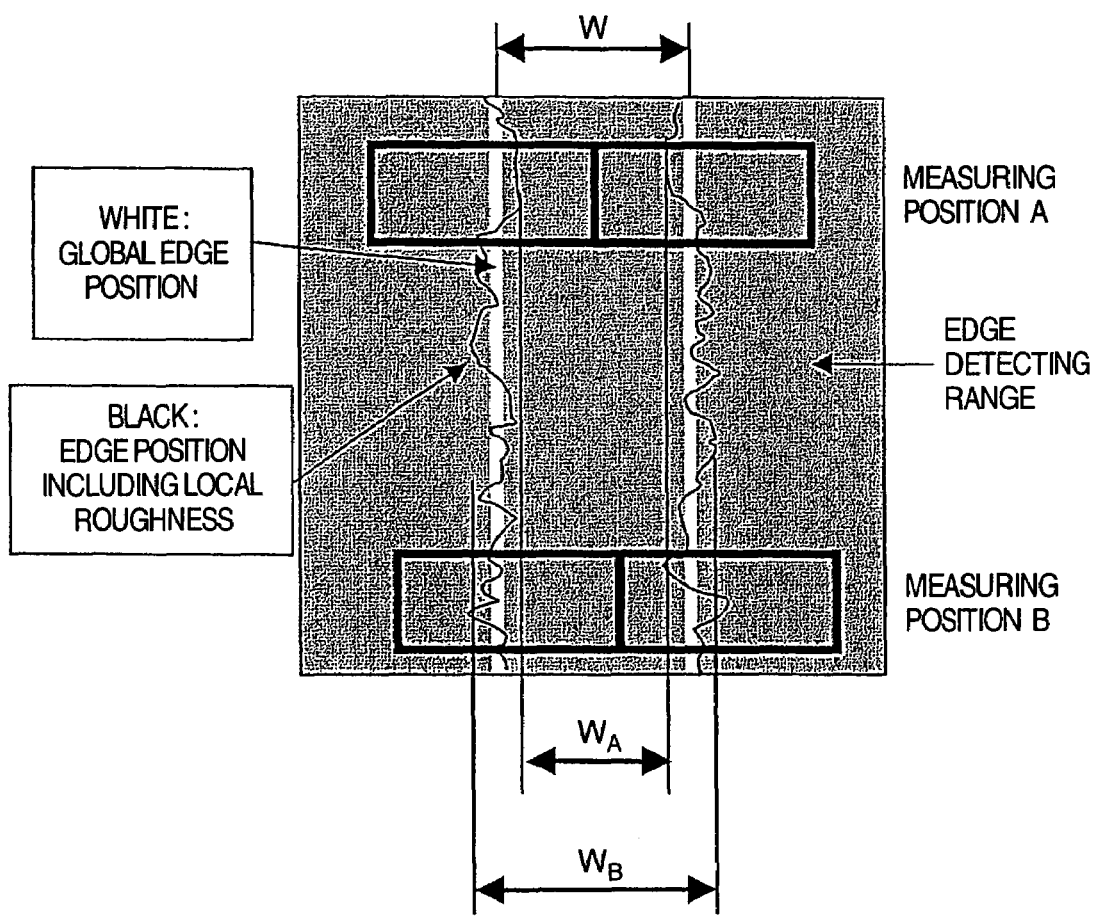
FIG. 3 is a diagram for explaining roughness.
Figure 4A:
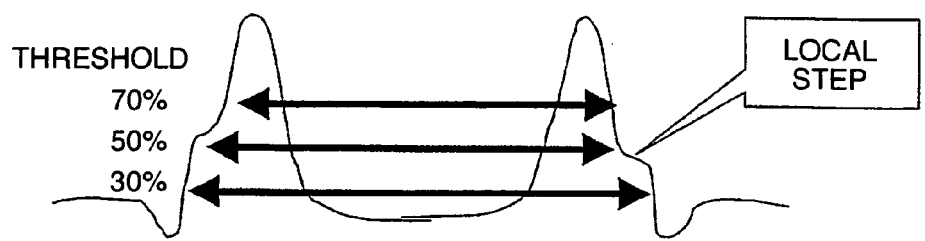
FIGS. 4A and 4B are diagrams showing exemplary profiles.
Figure 4B:
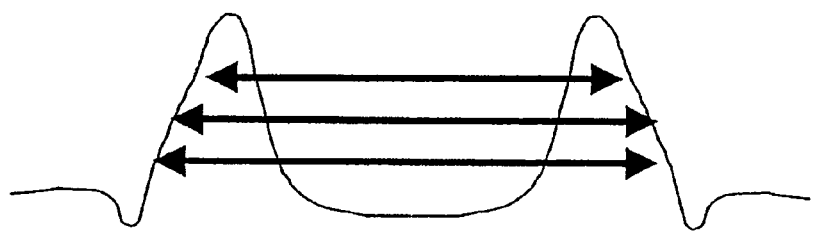
Figure 5A:
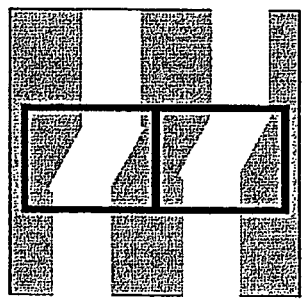
FIGS. 5A to 5D are diagrams showing patterns which are assumed for measurements.
Figure 5C:
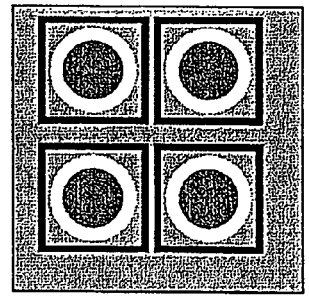
Figure 5B:
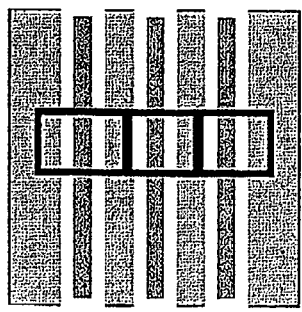
Figure 5D:
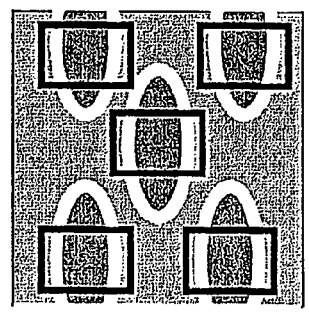

FIG. 1 is a schematic diagram illustrating an exemplary configuration of a scanning electron microscope for conducting a miniature pattern test according to the present invention. In an electron gun 3, a heating filament 2 is heated with a high voltage (500 volts or higher) to generate an electron beam 8. Subsequently, the electron beam 8 drawn out by a Wehnelt 4 is accelerated by an anode 5. This electron beam 8 is converged by a condenser lens 6, and is scanned in an arbitrary direction by a deflection signal generator 16 which is composed of a deflection coil 7, a scaling factor varying resistor 12, and a scanning power supply 16. Further, the electron beam 8 is focused by an object lens 9, and one-dimensionally or two-dimensionally scanned on a specimen 11 placed in a specimen chamber 10. Miniature patterns are engraved on the specimen 11. The irradiation of the electron beam 8 causes secondary electrons to be generated near the surface of the specimen 11 in an amount in accordance with the shape of the specimen 11. The secondary electrons are detected by a secondary electron detector 17. The detected secondary electrons are amplified by an amplifier 18 for transformation into a luminance modulation signal of a CRT 14. The CRT 14 is in synchronism with the deflection signal generator 16, so that the luminance modulation signal reproduces a secondary electron image generated by the electron beam 8 irradiated in synchronism from the surface of the specimen 11. Information on the surface of the specimen can be acquired through the foregoing procedure.

Figure 6:
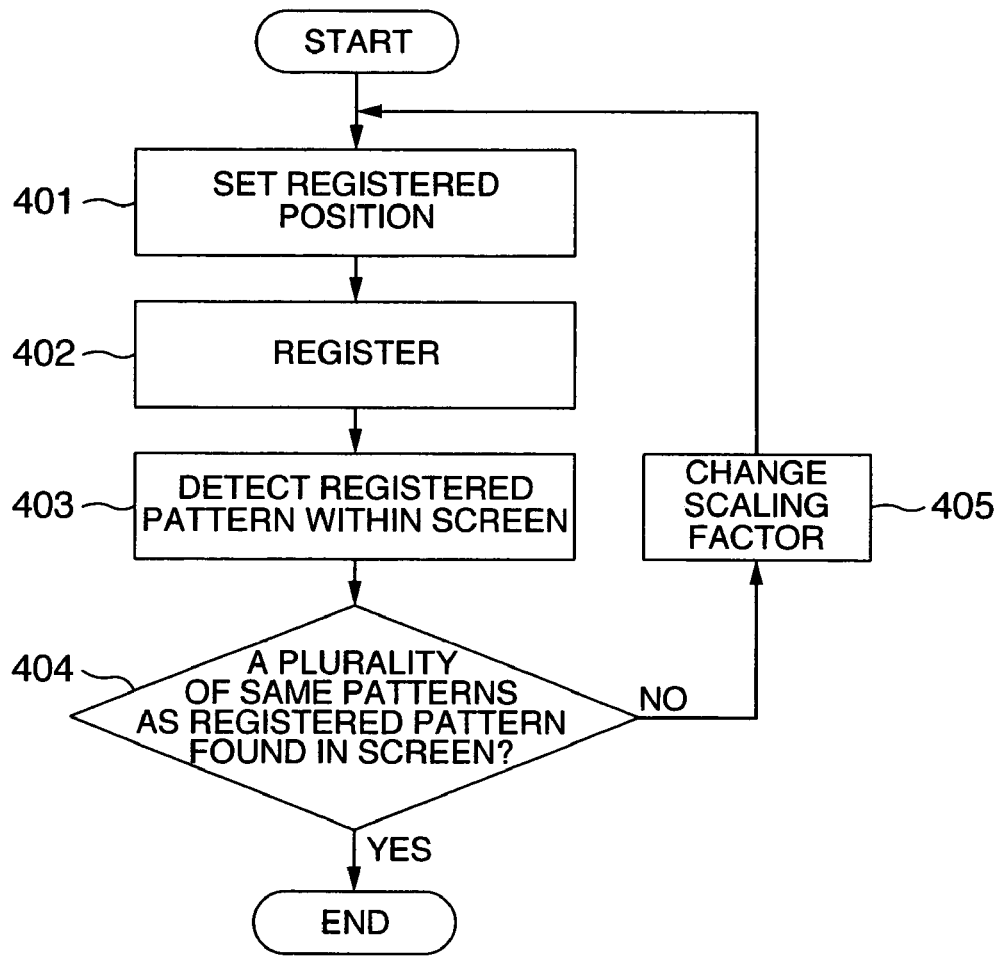
FIG. 6 is a flow chart illustrating the flow of a pattern measurement.

FIGS. 5A to 5D illustrate exemplary patterns which are assumed for measurement, and FIG. 6 illustrates the flow of a pattern measurement. As illustrated in FIGS. 5A to 5D, assume that a plurality of patterns under measurement repeatedly appear in the screen. As long as a plurality of patterns under measurement repeatedly appear in the screen, there is no particular limitations in the shape of pattern.

FIG. 6 illustrates a procedure for registering a measuring position within the screen. A scaling factor is set such that a plurality of repeated patterns under measurement appear within the same screen. Next, a registered position is set within the screen (401), and the position is registered (402). A confirmation is also made at this step as to whether or not a registered pattern has been correctly registered. When a portion without patterns is intentionally registered, this registration is treated as failed. Next, a detection is made as to whether or not a plurality of patterns are included in the screen (403). The registration procedure is terminated when a plurality of patterns are detected, whereas the scaling factor is reduced when a plurality of patterns are not detected (405), followed by a repetition of the execution from step 401 to step 404. Here, if a plurality of patterns do not appear within the screen even at a reduced scaling factor, the procedure is terminated, regarding as an error. When foreign substances or the like are registered in a region in which no patterns exist, the procedure is terminated, regarding as an error, because the same patterns are not found even at a reduced scaling factor.

Figure 7:
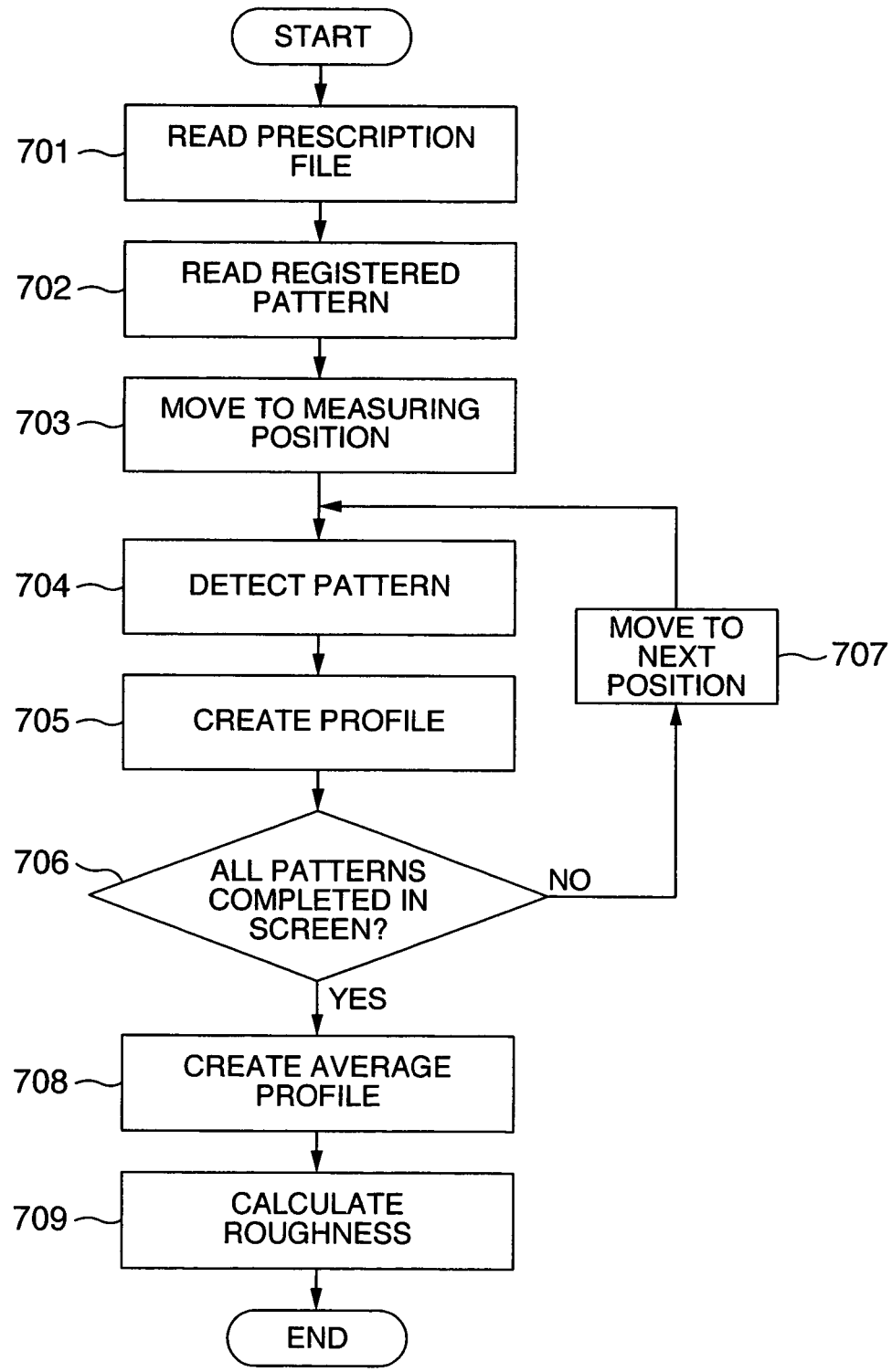
FIG. 7 is a flow chart illustrating a measuring procedure.

Next, FIG. 7 illustrates a prescription-based measuring procedure for making automatic measurements at a plurality of measuring positions within a wafer. The prescription is registered with coordinate information indicative of general measuring positions, a pattern (template) for finding a field of view through pattern matching after the field of view has been moved to the coordinates, relative positional information of a measuring area to the template, a measurement mode (a parameter for the measurement), and the like. There are two types of registered templates which include a template for finding the field of view at a low scaling factor, and a template for finding the field of view at a high scaling factor.

First, a prescription file which registers a pattern is read (701). Then, a registered pattern is read out (702), and is chosen for use in the pattern detection. Next, the field of view is moved to a measuring position (703). The same pattern as the template read at step 702 is detected at the measuring position (step 704). After the pattern detection, a profile is created for measuring positions based on the image (705). When the processing at step 704 and 705 has not been completed for all of a plurality of patterns found within the screen, the field of view is moved to the position of the next pattern (707), followed by a repetition of the processing from step 704 to step 706. After the profiles have been created for the plurality of patterns within the screen, an average profile is created (708). The average profile may be created by averaging all the created profiles, or by accumulating luminance values in the measuring area in the vertical direction (direction along the line) for each pattern under measurement to create a accumulated profile, and averaging the accumulated profile with the plurality of patterns.

Figure 8A:
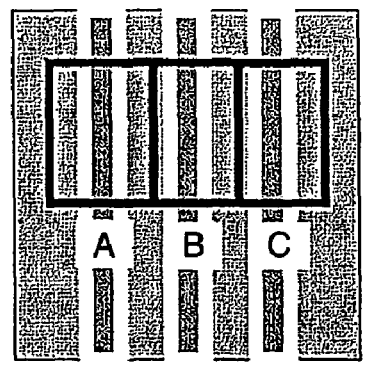
FIGS. 8A and 8B are diagrams illustrating an example of a measured line and space pattern.
Figure 8B:
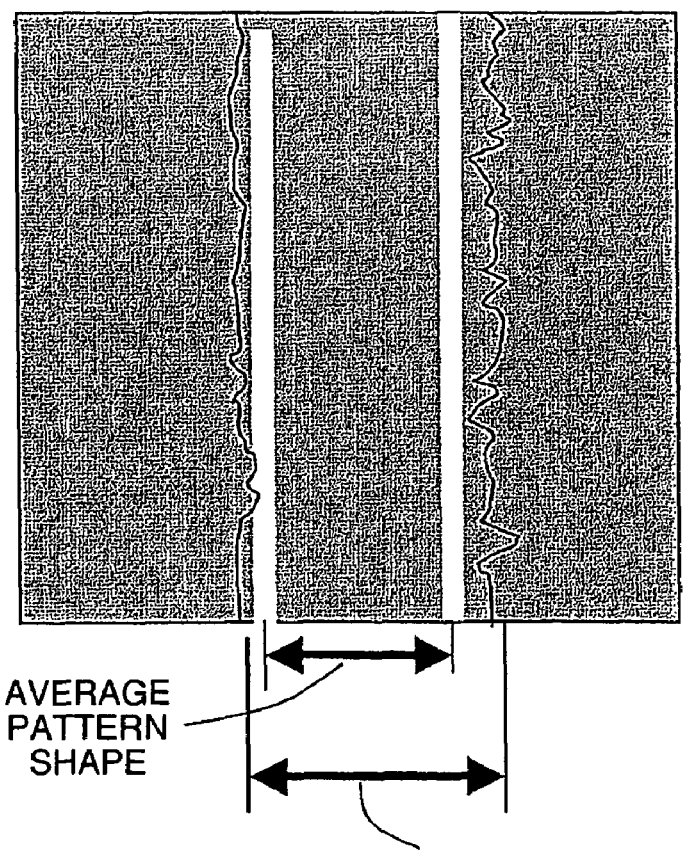

In a line and space pattern illustrated in FIGS. 8A, 8B, a profile is created in each of three measuring areas A, B, C, for example, as illustrated in FIG. 8A. The measuring areas A, B, C are defined longer in the vertical direction as indicated by black frames in FIG. 8A, and a plurality of profiles are created at regular intervals within the black frames. When edges are detected using the thus created profiles, a vertical pattern shape can be measured. Two black thin lines shown in FIG. 8B represent edge positions, i.e., a pattern shape, including local roughness measured, for example, in the measuring area A. Also, an average profile is calculated in the measuring areas A, B, C by superimposing all profiles created in the measuring areas A, B, C. Then, an average shape for a pattern averaged in the measuring areas A, B, C is found from the average profile. White lines in FIG. 8B represent the average shape of the pattern thus found. The average shape and roughness can be measured with a higher accuracy by statistically comparing the pattern shape measured in the measuring area A or the measuring area B, C, represented by the two black thin lines, i.e., the pattern shape (line width) found from the plurality of profiles created in the measuring area with the average pattern of all the patterns represented by white lines.

In regard to the measuring areas A, B, C, when they are identical in shape but different in design width, or when they have been previously known to be in a bad forming condition, similar calculations may be made by setting a contribution ratio to the average profile.

As described above, it is possible to measure variations in measurement depending on the pattern position by comparing a profile at each of measuring positions with an average profile. According to the method of the present invention, since an image can be captured at a lower scaling factor, damages to patterns can be reduced. Also, since a plurality of patterns can be measured from a single image, the method of the present invention helps improve the throughput. Further, since an average pattern is detected from a plurality of patterns identical in shape from a single image, it is possible to alleviate the influence of local edge roughness which can cause variations in measured values, and to quantify the tendency of the appearance of edge roughness by comparing the average pattern with each of pattern shapes at the respective positions.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. A method of measuring a shape of repetition patterns using a scanning electron microscope, comprising the steps of:
   setting a scaling factor of said scanning electron microscope which permits a plurality of repetition patterns to appear within a field of view;
   measuring shape of the repetition patterns included in the field of view and calculating an average value of the measured shape; and
   comparing the average value with shape roughness for the repetition patterns.

2. A pattern measuring method according to claim 1, wherein:
   said patterns under measurement include a line or a space pattern, and
   said step of measuring the shape includes:
      measuring width of a line or a space from the shape; and
      determining an average width of the line or the space from the average value to determine width roughness as the shape roughness.

3. A pattern measuring method according to claim 2, wherein said step of measuring the shape includes:
   accumulating luminance values in a shape measuring area for each of the patterns under measurement in a direction along the line or the space to create an accumulated profile, and
   averaging the accumulated profiles.

4. A pattern measuring method according to claim 1, wherein said average value to be calculated in said step of measuring the shape is determined by calculating an average value of values measured at a plurality of positions in a shape measuring area corresponding to each of the plurality of patterns under measurement.

5. A scanning electron microscope comprising:
   an electron source;
   a deflector for two-dimensionally scanning an electron beam emitted from said electron source; and
   a processing unit for measuring dimension of patterns on a sample;
   wherein said processing unit measures a shape of a plurality of repetition patterns included in a scanning area of the electron beam, calculates an average value of the measured shapes, and compares the average value with shape roughness for the repetition patterns.

6. A scanning electron microscope according to claim 5, wherein:
   said patterns under measurement include a line or a space pattern, and
   said processing unit measures width of the line or the space from the shape, and determines an average width of the line or the space from the average value to determine width roughness as the shape roughness.

7. A scanning electron microscope according to claim 6, wherein said processing unit accumulates luminance values in the scanning area of the electron beam for each of the patterns under measurement in a direction along the line or the space to create an accumulated profile and to average the accumulated profiles.

8. A scanning electron microscope according to claim 5, wherein said processing unit determines the average value by calculating an average value of values measured at a plurality of positions in the scanning area of the electron beam corresponding to each of the plurality of patterns under measurement.

9. A scanning electron microscope comprising:
an electron source;
a deflector for two-dimensionally scanning an electron beam emitted from said electron source; and
a processing unit for measuring dimension of patterns on a sample;
wherein said processing unit determines measurement values of a plurality of repetition patterns included in a scanning area of the electron beam and calculates an average value of the measurement values on the basis of design width of the plurality of patterns or forming condition of the plurality of patterns.

10. A scanning electron microscope according to claim 9, wherein said processing unit compares the average value with roughness for the repetition patterns.

* * * * *